(12) United States Patent
Xue et al.

(10) Patent No.: US 6,920,198 B2
(45) Date of Patent: Jul. 19, 2005

(54) METHODS AND APPARATUS FOR PROCESSING A FLUOROSCOPIC IMAGE

(75) Inventors: Ping Xue, Cottage Grove, WI (US); Kenneth Scott Kump, Waukesha, WI (US); Brian David Yanoff, Schenectady, NY (US); Richard Aufrichtig, Mountain View, CA (US); Mylene Roussel, Saint Germain les Arpajon (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/428,734

(22) Filed: May 2, 2003

(65) Prior Publication Data

US 2004/0218729 A1 Nov. 4, 2004

(51) Int. Cl.[7] ............................................. G01N 23/083
(52) U.S. Cl. ........................ 378/62; 378/98.3; 378/98.8
(58) Field of Search ........................ 378/62, 98.2, 98.3, 378/98.8

(56) References Cited

U.S. PATENT DOCUMENTS

| 4,482,918 A | 11/1984 | Keyes et al. |
| 4,752,944 A | 6/1988 | Conrads et al. |
| 4,848,879 A | 7/1989 | Nishimura et al. |
| 4,975,935 A | 12/1990 | Hillen et al. |
| 5,047,631 A | 9/1991 | Frese |
| 5,272,536 A | 12/1993 | Sudo et al. |
| 5,331,682 A | 7/1994 | Hsieh |
| 5,493,598 A | 2/1996 | Yassa et al. |
| 5,563,421 A | 10/1996 | Lee et al. |
| 5,608,205 A | 3/1997 | Bird et al. |
| 5,771,272 A | 6/1998 | Berger et al. |
| 5,969,360 A | 10/1999 | Lee |
| 5,999,587 A | 12/1999 | Ning et al. |
| 6,259,084 B1 | 7/2001 | Kochis et al. |
| 6,404,853 B1 | 6/2002 | Odogba et al. |
| 2003/0055573 A1 * | 3/2003 | LeGore et al. ................. 702/26 |
| 2004/0258207 A1 * | 12/2004 | Okamura et al. .......... 378/98.8 |

FOREIGN PATENT DOCUMENTS

| EP | 1113293 A2 | 7/2001 |
| FR | 2831013 | 4/2003 |

OTHER PUBLICATIONS

U.S. patent application of Albagli et al., for "Method and Apparatus for Processing a Fluoroscopic Image," Ser. No. 09/977,474, filed Oct. 15, 2001.

Foreign Search Report for French Application 0404402, Mailed Nov. 18, 2004.

* cited by examiner

Primary Examiner—David V Bruce
(74) Attorney, Agent, or Firm—Carl B. Horton, Esq.; Armstrong Teasdale LLP

(57) ABSTRACT

A method for processing a fluoroscopic image includes generating a lag prediction model, scanning an object at a first radiation dosage with an imaging system including at least one radiation source and at least one detector array, and periodically updating the lag prediction model during the scan to generate at least one fluoroscopic image of the object.

28 Claims, 5 Drawing Sheets

LAG FROM DSA APPLICATIONS WITH DIFFERENT DOSE LEVEL IS DECAYED AS A FUNCTION OF TIME IN X-RAY FLUORO.

NORMALIZED LAG RESIDUE IS PLOTTED AS A FUNCTION OF TIME AND DETECTOR ENTRANCE DOSE IN RAD EXPOSURES.

EFFECT OF WEIGHTING COEFFICIENT VALUE ON THE VISIBILITY OF FLUORO TO FLUORO LAG: (A) IMAGE WITHOUT LAG CORRECTION, (B) IMAGE CORRECTED WITH WA=WB=1 (EQUIVALENT TO NO WEIGHTING COEFFICIENTS), (C) IMAGE CORRECTED WITH WA=wB= 0.5.

LOCATION OF LAG RESIDUE ON AN IMAGE VARIED WITH DETECTOR FOV SETTINGS.

METHODS AND APPARATUS FOR PROCESSING A FLUOROSCOPIC IMAGE

BACKGROUND OF THE INVENTION

This invention relates generally to imaging systems and more particularly to methods and apparatus for processing a fluoroscopic image.

In at least some known imaging systems, a radiation source projects a cone-shaped beam which passes through the object being imaged, such as a patient and impinges upon a rectangular array of radiation detectors.

In some known radiation detectors, such as those including thin film transistors (TFTs) and photodiodes, a "lag" signal may occur. Lag is a dependence of an image signal due to the past exposure history. Some known medical applications require a transition from a high radiation dosage exposure to a fluoroscopic mode, which uses a low radiation dosage exposure. A lag signal from the high radiation dosage exposure may introduce artifacts into the fluoroscopic images in the form of ghost images of the high exposure image.

For example, detector lag can occur when an x-ray imaging system is switched from a high dose exposure application, such as Cine Record (Record), Digital Subtraction Angiography (DSA), and Radiography (RAD), to a low dose fluoroscopy (Fluoro) in a relatively short period. Additionally, at least one clinical study has shown that lag can persist in a Fluoro sequence for up to approximately several minutes. Accordingly, lag residue also facilitates reducing a dynamic range of an x-ray signal and a signal contrast.

BRIEF SUMMARY OF THE INVENTION

In one aspect, a method for processing a fluoroscopic image is provided. The method includes generating a lag prediction model, scanning an object at a first radiation dosage with an imaging system including at least one radiation source and at least one detector array, and periodically updating the lag prediction model during the scan to generate at least one fluoroscopic image of the object.

In another aspect, a medical imaging system for processing a fluoroscopic image is provided. The medical system includes a flat panel detector array, at least one radiation source, and a computer coupled to the flat panel detector array and the radiation source. The computer is configured to generate a lag prediction model, scan an object at a first radiation dosage with an imaging system including at least one radiation source and at least one detector array, and periodically update the lag prediction model during the scan to generate at least one fluoroscopic image of the object.

In a further aspect, a computer is provided. The computer is programmed to generate a lag prediction model, scan an object at a first radiation dosage with an imaging system including at least one radiation source and at least one detector array, and periodically update the lag prediction model during the scan to generate at least one fluoroscopic image of the object.

In a still further aspect, a method for processing a fluoroscopic image is provided. The method includes receiving a first dosage for a first scan of an object, scanning the object with the received first dosage, generating at least one dark image, generating at least one lag prediction image based on the dark image, receiving a second dosage for a second scan of the object, retrieving at least one stored parameter based on the received second dosage, and incorporating the retrieved parameter into the lag correction model.

DETAILED DESCRIPTION OF THE INVENTION

Figure 1:
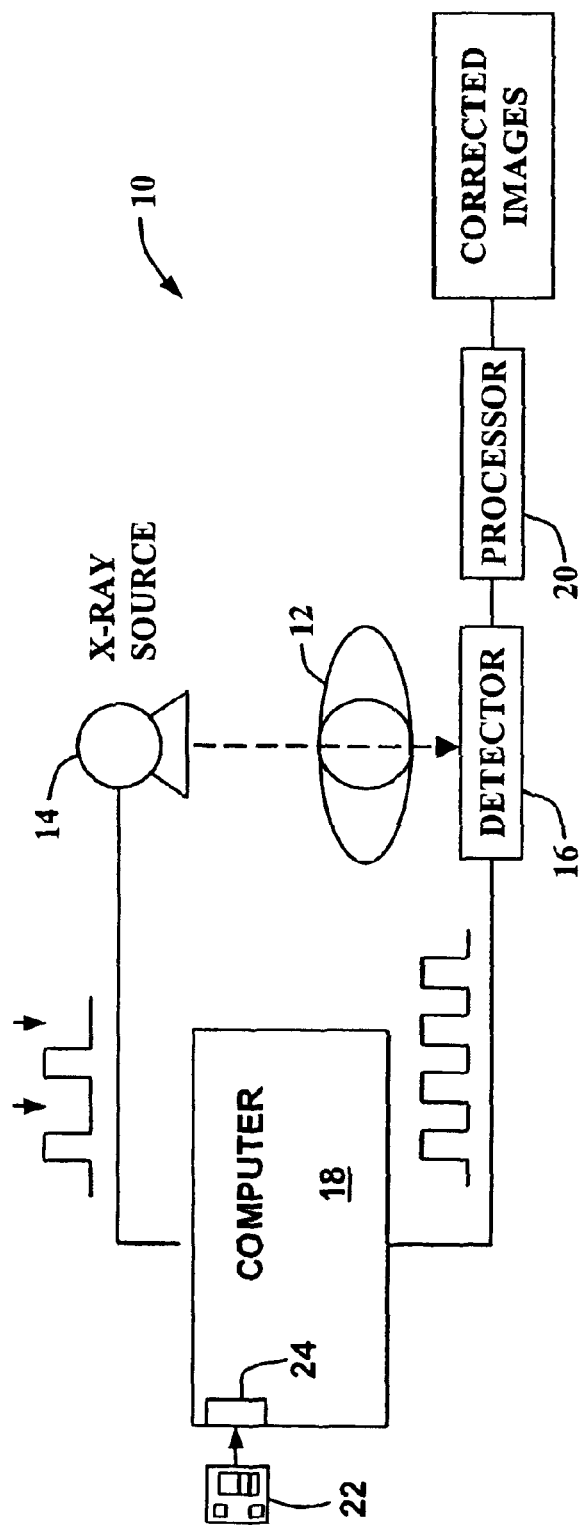
FIG. 1 is a pictorial view of an imaging system.

Referring to FIG. 1, and in an exemplary embodiment, a digital imaging system 10 generates a plurality of two dimensional images representative of an imaged object 12, such as, but not limited to, performing diagnosis of an object of interest, e.g., a patient's heart in cardiac fluoroscopy. System 10 includes a radiation source 14, such as an x-ray source 14, and at least one detector array 16 for collecting projection data. Specifically and in one embodiment, system 10 includes a radiation source 14 which projects a cone-shaped beam of x-rays which pass through object 12 and impinge on detector array 16. Detector array 16 is fabricated in a flat panel configuration having a plurality of pixels (not shown) arranged in rows and columns so that an image is generated for an entire object of interest such as heart 12. Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces an electric signal that represents the intensity, after attenuation by object 12, of an x-ray beam impinging on detector array 16.

The operation of radiation source 14 is controlled by a computer 18. Computer 18 provides power and timing signals to radiation source 14 and detector 16. In one embodiment, computer 18 includes an image processor 20. Alternatively, computer 18 and processor 20 can be separate components. Image processor 20 receives sampled and digitized radiation data from detector 16 and performs high-speed image processing, as described herein. The processed two-dimensional image, representative of imaged object 12, is applied as an input to a computer 18. In one embodiment, computer 18 includes a device 22, for example, a floppy disk drive or CD-ROM drive, for reading instructions and/or data from a computer-readable medium 24, such as a floppy disk or CD-ROM. In another embodiment, computer 18 executes instructions stored in firmware (not shown). Computer 18 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In use, a patient is positioned so that the object of interest 12 is within the field of view of system 10, i.e., heart 12 is positioned within the imaged volume extending between radiation source 14 and detector array 16. Images of heart 12 are then acquired to generate a plurality of radiographic images or fluoroscopic images of the volume of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Additionally, although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 2:
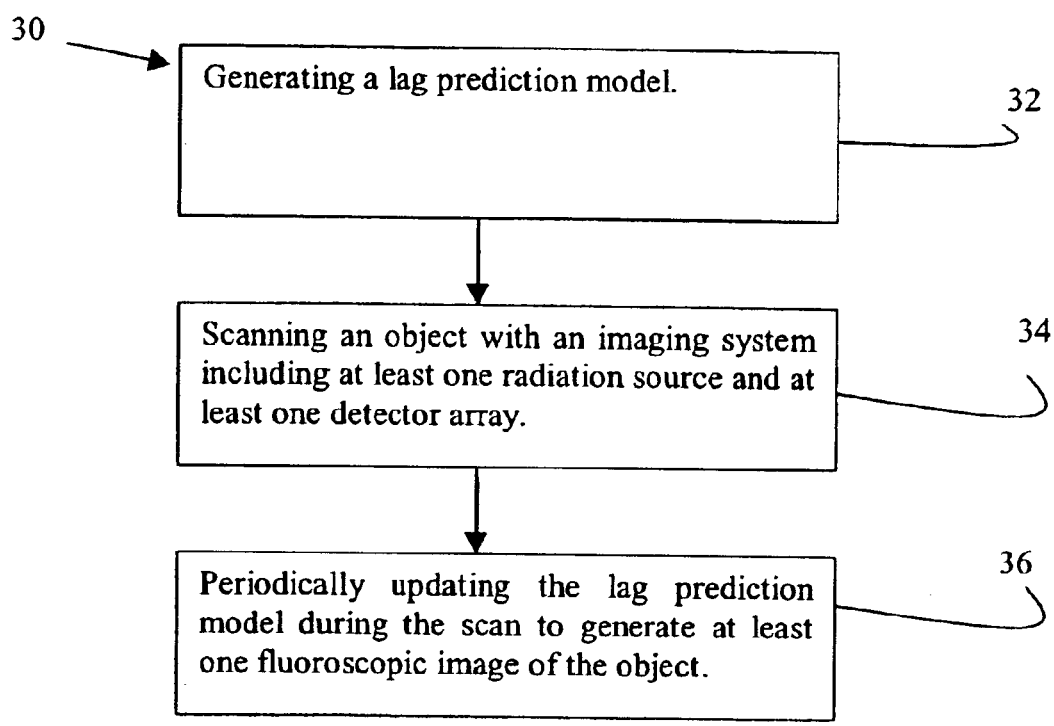
FIG. 2 is a flow chart illustrating an exemplary method for processing a fluoroscopic image.

FIG. 2 is a flow diagram illustrating a method 30 for processing a fluoroscopic image, wherein the method includes generating 32 a lag prediction model, scanning 34 an object 12 (shown in FIG. 1) with an imaging system 10 (shown in FIG. 1) including at least one radiation source 14 (shown in FIG. 1) and at least one detector array 16 (shown in FIG. 1), and periodically updating 36 the lag prediction model during the scan to generate at least one fluoroscopic image of object 12.

Figure 3:
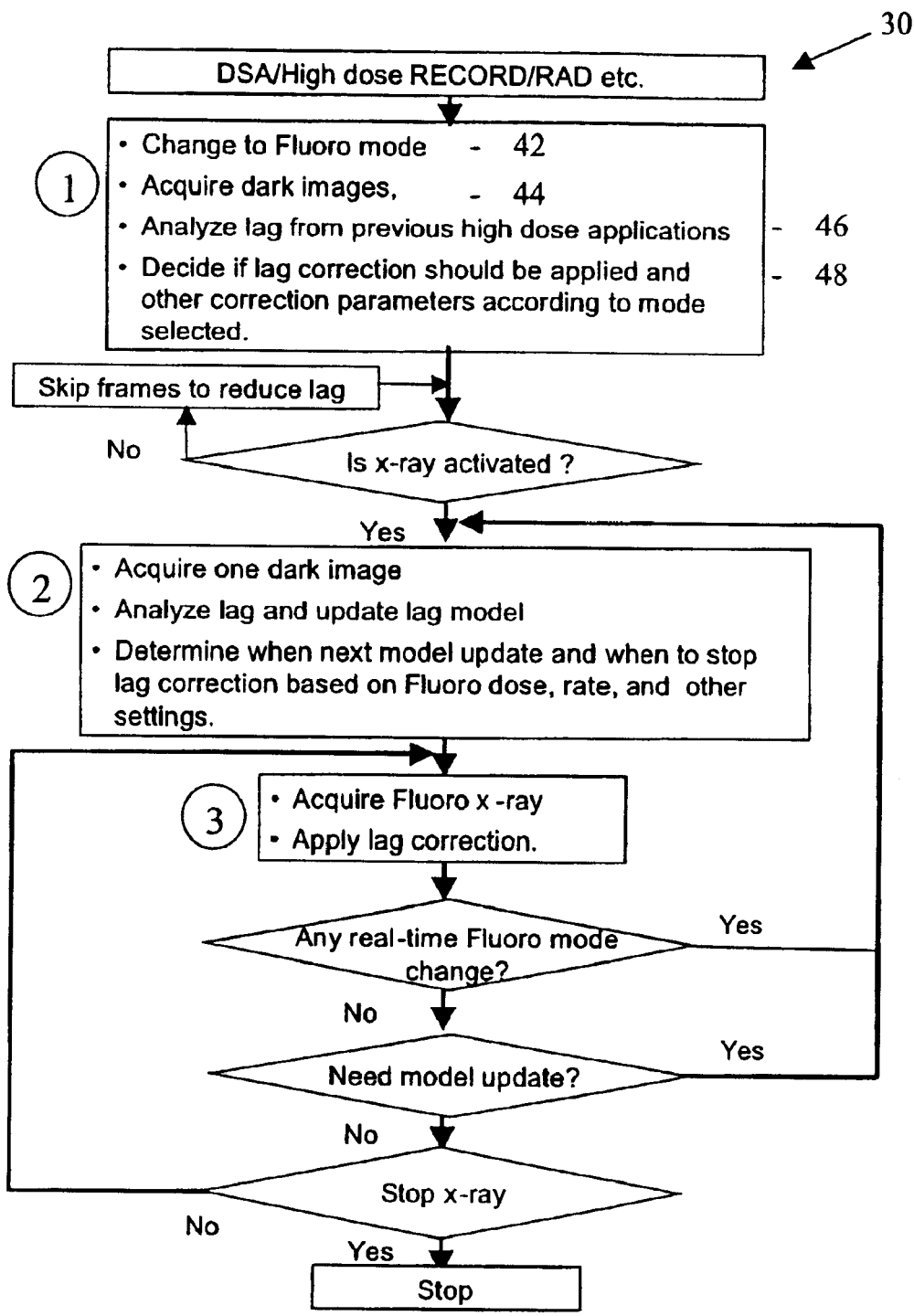
FIG. 3 is a graphical representation of an exemplary embodiment of the method described in FIG. 2.
Figure 4:
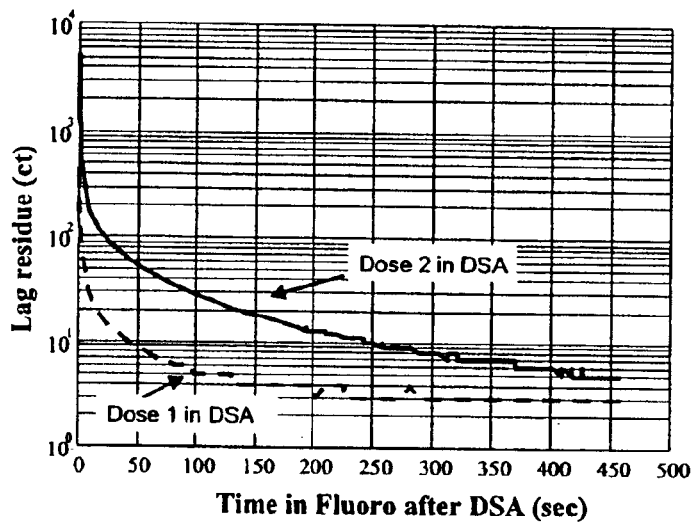
FIG. 4 illustrates an exemplary detector lag in log-linear space.

FIG. 3 is a more detailed flowchart of the method shown in FIG. 2. FIG. 4 illustrates an exemplary detector lag in log-linear space. As shown in FIG. 4, lag from a high dosage applications with differing dosage levels decays at a differing rate and may last for several minutes, therefore pixel by pixel calculations are used to determine the lag. Accordingly, generating 32 a lag prediction model includes operating imaging system 10 in a high dose application mode, such as but not limited to, Cine Record (Record) mode, Digital Subtraction Angiography (DSA) mode, and Radiography (RAD) mode, and then switching 44 to Fluoro mode. After an operator has switched the imaging system to Fluoro mode, a plurality of dark images is acquired. In one embodiment, generating 32 a lag prediction model includes acquiring 44 at least one dark image in the Fluoro mode, analyzing 46 the at least one dark image to determine if the at least one dark image include a lag signal, and determining 48 if a lag correction should be applied based on the at least one dark image.

In use, imaging system 10 is operated in the high dose application mode and then switched to the fluoroscopic mode. At least two dark images representative of lag residue present after operating in the high dose application mode are then acquired. Acquiring a dark or offset image in the absence of x-ray and light represents a dark scan, and results in a signal that is slightly negative. This negative charge is "retained" by a photodiode in a detector array, such as detector array 16 (shown in FIG. 1), when it is initiated or scanned. Retained charges "leak out" slowly over time and add a positive signal to pixels that are read subsequently. A lag model is then estimated using the at least two dark images to predict lag in subsequent x-ray images.

In the exemplary embodiment, generating 32 a lag prediction model includes modeling the lag using a linear function wherein a quantity of image acquisitions or a time in log-log space can be used as variables. For example, a lag prediction model can be modeled in accordance with:

$$\log_e(\text{lag}) = A + B * \log_e(fr), \text{ or} \quad (1)$$

$$\log_e(\text{lag}) = A + B * \log_e(T), \quad (2)$$

where

A is a first model array parameter,

B is a second model array parameter, fr is frame number starting from the last high dose exposure that produces lag, and T is time starting from last high dose exposure that produces lag.

Although a lag prediction model shown is calculated using a base-e, it should be understood, that the lag prediction model can be calculated using a plurality of bases, such as, but not limited to, a base-10 logarithm and a base-2 logarithm. When the predicted lag is converted back to a linear scale, it is important that the same base is used for the exponentiation.

In the exemplary embodiment, the first model parameter A and the second model parameter B are calculated independently for each pixel of the image. Accordingly, A and B are each 2D arrays with a 1-to-1 correspondence to the pixels in the original image. Since at least two 2D array parameters are used to generate the lag prediction model, at least two dark images that include lag information at different frames or times are used to estimate the first model array parameter (A), and the second model array parameter (B). For example, using two dark images that include lag, $\text{lag}_1$, and $\text{lag}_2$, the model parameters A and B are determined in accordance with:

$$A = \log_e(lag_2) - \frac{\log_e(lag_1/lag_2)}{\log_e(T_1/T_2)} * \log_e(T_2), \text{ and} \quad (3)$$

$$B = \frac{\log_e(lag_1/lag_2)}{\log_e(T_1/T_2)}, \quad (4)$$

where $T_1$ is first time at which a dark image including lag is acquired, and $T_2$ is a second time a dark image including lag image is acquired.

The lag prediction model predicting lag at time T, wherein ($T > T_1$ and $T_2$), is determined in accordance with:

$$\text{lag'} = \exp[A + B * \log_e(T)], \quad (5)$$

and lag correction is performed in accordance with;

$$(\text{Corrected Image}) = (\text{Original Image with lag}) - \text{lag'} \quad (6)$$

Accordingly, and referring to FIG. 3, when imaging system 10 completes operation in the high dose application, imaging system 10 switches detector 16 to Fluoro mode, acquires at least two dark images, and generates a lag prediction model using the at least one dark image.

After determining 48 if a lag correction should be applied based on the at least two dark images, system 10 determines if x-ray source 14 has been activated, i.e. whether a patient is currently being scanned. If a patient is not being scanned then additional dark images are acquired to reduce the lag. When x-ray source 14 is activated in Fluoro mode, i.e. scanning 34 object 12 with imaging system 10, a single dark image is acquired. The single dark image is used to analyze current lag and update the lag prediction model parameters A and B. Additionally, the single dark image is used to determine when the lag prediction model should be updated, and when to stop lag correction based on at least one of a Fluoro dose and a frame rate. System 10 then acquires a plurality of x-ray images and applies the lag correction to each image. Additionally, the lag prediction model is updated periodically by acquiring another dark image during scanning by inhibiting one frame of x-ray, and using the dark image to update the model parameters A and B.

Figure 5:
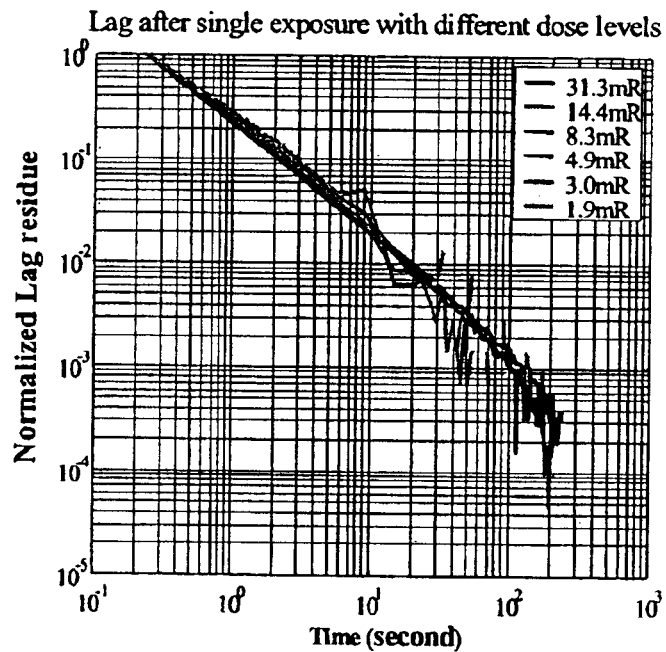
FIG. 5 illustrates a normalized lag in log-log space.

More specifically, to estimate the model parameters for the model listed in equations (1) and (2), at least two dark images are acquired. In the exemplary embodiment, the variation of estimated parameters is increased with the decrease of difference of lag residues between two offsets due to image noise. To generate a robust estimate and facilitate reducing additional noise due to modeling, the difference between lag residues in the two dark images is maximized. For example, instead of updating two dark images continuously, a single dark image that includes a relatively high lag residue is acquired at the beginning of the Fluoro mode, and the second dark image is updated using at least one of a time and a Fluoro frame number. Since lag is almost constantly decayed in a log-log space as shown in FIG. 5, the methods described herein will not introduce significant modeling error while facilitating noise reduction, fast access to Fluoro due to Fluoro mode or FOV change. Since only one dark image is used to update the model, lag correction potentially affects normal Fluoro access time and FOV transition by only one frame delay at given frame rate such as 30 or 15 frame per second.

Because lag introduced by non-uniform exposure varies pixel by pixel, the above described correction is calculated on a pixel by pixel basis. Therefore, the same parameter value to present lag magnitude for different pixels is not used. Additionally, the slope of lag in log-log space is approximately constant across different pixels on lag images although lag magnitudes are different due to different dose levels across x-ray field in previous exposures. For example, FIG. 5 shows the normalized lag as a function of dose in previous exposures and time in log-log space. Accordingly, as illustrated in FIG. 5 a single model parameter, such as, but not limited to, B, is used to present the slope of lag decay in the model prediction. Using a single model parameter to update the lag prediction model facilitates reducing a computation time for lag correction in system 10. Using a single model parameter to update the model prediction also facilitates eliminating individual, pixel-by-pixel multiplication in the model update and lag correction. Using a single model parameter to update the model prediction also facilitates the ability to read out pipeline calculations from the detector data read to complete the model update and lag correction. In another exemplary embodiment, a single, maximum lag residue on images is used to estimate a single slope parameter, such as B, in a lag model. Using a single, maximum lag residue facilitates reducing the computation time, image noise, and noise in image area that does not include lag residue. In use, the actual highest lag residue is estimated based on bad pixel corrected/excluded images.

Figure 6:
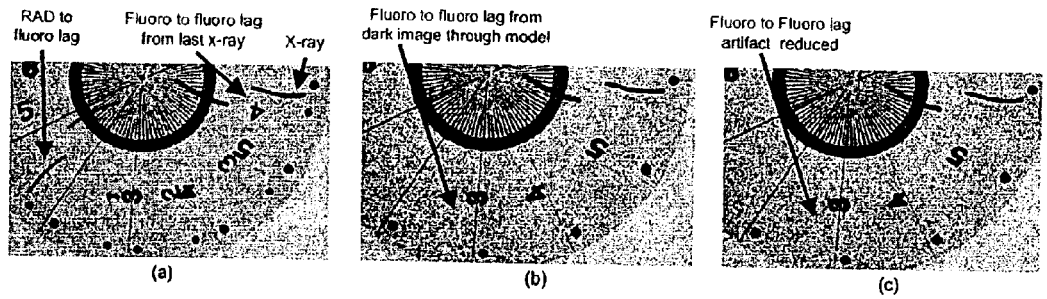
FIG. 6 is a pictorial view of images acquired using a weighting coefficient.

In another exemplary embodiment, method 30 includes using at least one weighting coefficient to facilitate reducing an effect of a modeling noise. For example, using coefficients, $w_A$ and $w_B$, model parameter A and B are estimated in accordance with:

$$A_{new}=(1-w_A)*A_{old}+w_A*A_{current} \quad (7)$$

$$B_{new}=(1-w_B)*B_{old}+w_B*B_{current} \quad (8)$$

where $A_{current}$ and $B_{current}$ are estimated from equations (3) and (4). For example, if $w_A=w_B=0.5$, approximately 50% of the noise can be removed from the model propagation. Additionally, using weighting coefficients facilitates reducing the effect of Fluoro lag on lag corrected images, as shown in FIG. 6.

In another exemplary embodiment, a period length for the lag model is updated while operating in Fluoro acquisition mode. In use, at least one x-ray free, dark image is acquired while operating in Fluoro mode. Therefore, imaging system 10 skips one x-ray acquisition which may result in an unsteady rhythm while viewing the images. Accordingly, and in one embodiment, method 30 also include defining a period M between two frames acquired using an active x-ray source, and varying the period M to facilitate reducing the unsteady viewing rhythm due to the gap caused by taking the dark image. For example, since lag decays in almost constant speed in log-log space, the period M is gradually increased as an exponential function to maintain an approximately constant correction error. Alternatively, the period M can be adjusted using a Look-up-table (LUT) that uses a mathematical function to compensate for a plurality of operating conditions, such as, but not limited to, Fluoro signal/noise level, critical phase during the beginning and/or middle of Fluoro, and initial lag residue level. In another embodiment, the period M can be configured to operate in at least one of a Pulsed Fluoro mode and a Continuous Fluoro mode when $M_O=\infty$, i.e., no dark image is acquired while operating imaging system 10 in Fluoro mode.

Figure 7:
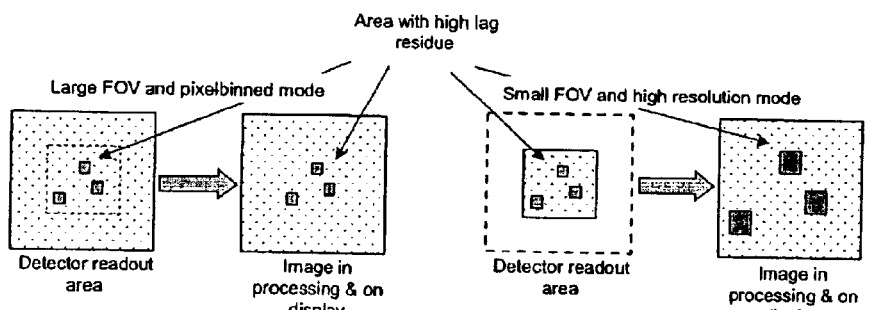
FIG. 7 illustrates a detector readout with a varied Field of View (FOV).

In another exemplary embodiment, generating 32 a lag prediction model includes acquiring a single dark image, and using the single dark image to generate the lag prediction model. For example, changing from a first fluoroscopic mode to a second fluoroscopic mode may result in different detector gain settings. Additionally, to achieve real-time image acquisition and processing, a field of view (FOV) change may cause detector readout with different pixel size and different area as shown in FIG. 7. Lag residue from previous high dose exposure is also varied with detector gain settings corresponding to different Fluoro modes. Accordingly, the methods described herein facilitate compensating for a difference if two dark images are acquired with different gains. Additionally, if two dark images for model update are acquired with different pixel size and a different area due to the different FOV, the detector in an image area that matches lag at the same physical detector position is resampled.

In use, after a high dose exposure, a first dark image, $L_1$, for the lag model is acquired using a maximum detector imaging size. A second dark image, used to update the lag model, is acquired prior to changing the Fluoro mode associated with at least one of, a specific detector setting, a FOV readout, and a detector gain. The first dark image is re-sampled to have the same size as the second dark image related to the specific FOV and selected resolution. The first dark image is then scaled by a ratio of the two electronic gains, $G_1$ and $G_2$, used to acquire the first dark image and the second dark image. In use, the first lag image $L_1$ is used to generate a modified first lag image $L_1$ in accordance with $$L'_1 = resampled\left\{L_1 * \frac{G_2}{G_1}\right\}. \quad (9)$$

Using the modified first lag image $L_1$, and the second lag image $L_2$, the lag can be estimated and used to update the lag model for lag correction in subsequent x-ray Fluoro images. When the detector setting is changed to a different Fluoro mode, only one dark image is then used to update the lag model.

As explained previously herein, lag generates a plurality of undesirable characteristics in Fluoro images, such as, but not limited to, a dynamic range reduction, a signal contrast reduction, and artifacts when the imaged object moves during scanning. Generally, lag artifacts are the most undesirable characteristic introduced in the fluoro images. The effect of lag artifact shown on the fluoro image is background signal dependent. Therefore, the effect is decreased as a function of one over the square root of the detector entrance dose.

In the exemplary embodiment, system 10 includes a real-time, automatic dose control mechanism which is used to generated a real-time dose feedback. In one embodiment, the real-time dose feedback is used to determine a duration to apply the lag correction to the fluoro image sequence. In another embodiment, the real-time dose feedback is used for real-time optimization. For example, the lag correction parameters (A and B) are optimized based on a pre-selected Fluoro mode prior to scanning using a low dosage application. Optimizing the lag correction parameters facilitates decreasing the lag correction time when operating system 10 in a high dose Fluoro mode. Additionally, optimizing the lag correction parameters facilitates determining whether a lag correction is applied to the fluoro images, and also increases the duration between model updates thereby reducing the unsteady rhythm of the fluoro images that may be noticeable while viewing the fluoro images.

In another exemplary embodiment, lag correction is optimized based on the application, such as Fluoro or DSA. For example, if a patient in the x-ray field is repositioned during transition between DSA to Fluoro, then the lag artifact could be more easily observed than when there is a relatively small amount of motion when transitioning between Fluoro and DSA. Therefore, the tolerance for error residue after lag correction and the threshold for stopping lag correction are different and can be varied from application to application.

The method described above can be implemented in an x-ray system for real-time (30 frame/sec) image acquisition. Additionally, the lag correction model is more robust and has minimal impact on an image area that does not include lag. The algorithm introduces less noise due to image subtraction. It also provides fast transition from DSA/Record/RAD etc. to Fluoro, fast transition between different Fluoro modes, and fast transition between different detector readout in different regions of interest on full size of imager and in different resolutions.

The methods described herein facilitate maximizing the ratio of lag residue and noise in the algorithm design to improve robustness, and facilitate using a single parameter to represent the slope of lag decay, thereby reducing the computation time and the effect of lag correction on image area without lag. Additionally, using the weighting coefficient for model parameters facilitates reducing noise through the lag model and lag subtraction, and facilitates varying the period length for model update in Fluoro acquisition based on lag residue and Fluoro dose or signal-to-noise ratio to reduce the effect of unsteady rhythm while viewing the images. Finally, the methods described herein facilitate automatic gain and re-sampling adjustment of one dark image for fast transition between different FOV, detector settings related to Fluoro mode change, and optimizing the correction algorithm and configurable parameters based on at least one of the Fluoro dose, the frame rate, and the application.

While the invention has been described in terms of various specific embodiments, those skilled in the art will recognize that the invention can be practiced with modification within the spirit and scope of the claims.

What is claimed is:

1. A method for processing a fluoroscopic image, said method comprising:

generating a lag prediction model;

scanning an object at a first radiation dosage with an imaging system including at least one radiation source and at least one detector array; and periodically updating the lag prediction model during the scan to generate at least one fluoroscopic image of the object.

2. A method in accordance with claim 1 wherein said generating a lag prediction model comprises:

scanning the object at a second radiation dosage greater than the first radiation dosage;

generating at least two dark images after scanning the object with the second radiation dosage; and using the at least two dark images to generate the lag prediction model.

3. A method in accordance with claim 1 further wherein said periodically updating the lag prediction model comprises:

acquiring at least one dark image; and updating the lag prediction model using the at least one dark image.

4. A method in accordance with claim 1 further wherein said periodically updating the lag prediction model comprises:

acquiring only one dark image; and updating the lag prediction model using the only one dark image.

5. A method in accordance with claim 1 wherein said generating a lag prediction model comprises generating a lag prediction model in accordance with:

$$Image_{corr} = Image_{w\_lag} - lag';$$

where:

Image $_{w\_lag}$ is a current fluoro image;

$$lag' = \exp[A + B * \log_e(T)];$$

A is a first model parameter,

B is a second model parameter; and

T is a time beginning from the last high dose exposure that produces lag.

6. A method in accordance with claim 2 wherein said generating at least two dark images after scanning the object comprises generating a plurality of dark images separated in time by a varying time period.

7. A method in accordance with claim 5 further comprising applying a weighting function to the first model parameter and the second model parameter.

8. A method in accordance with claim 5 further comprising:
determining a first model parameter A in accordance with:

$$A = \log_e(lag_2) - \frac{\log_e(lag_1/lag_2)}{\log_e(T_1/T_2)} * \log_e(T_2);$$

and
determining a second model parameter in accordance with:

$$B = \frac{\log_e(lag_1/lag_2)}{\log_e(T_1/T_2)};$$

where:
$T_1$ is first time at which a dark image including lag is acquired;
$T_2$ is a second time at which a dark image including lag image is acquired.

9. A method in accordance with claim 1 further comprising:
generating a first modified lag image $L'_1$ in accordance with:

$$L'_1 = resampled\left\{L_1 * \frac{G_2}{G_1}\right\};$$

where:
$L'_1$=is the modified lag image;
$L_1$=is a first dark image having a lag residue signal;
$G_1$ is a first detector gain; and
$G_2$ is a second detector gain;
generating a second lag image $L_2$; and
using the first modified lag image and the second lag image to periodically update the lag prediction model.

10. A method for processing a fluoroscopic image, said method comprising:
scanning an object at a second radiation dosage with an imaging system including at least one radiation source and at least one detector array;
generating at least one dark image after scanning the object with the second radiation dosage;
using the at least two dark images to generate a lag prediction model;
scanning the object at a first radiation dosage;
acquiring at least one dark image during the scan at the first radiation dosage; and
periodically updating the lag prediction model during the scan using the at least one dark image to generate at least one fluoroscopic image of the object.

11. A medical imaging system for processing a fluoroscopic image, said medical system comprising:
a flat panel detector array;
at least one radiation source; and
a computer coupled to said flat panel detector array and said radiation source, said computer configured to:
generate a lag prediction model;
scan an object at a first radiation dosage with an imaging system including at least one radiation source and at least one detector array; and
periodically update the lag prediction model during the scan to generate at least one fluoroscopic image of the object.

12. A medical imaging system in accordance with claim 11 wherein to generate a lag prediction model, said computer further configured to:
scan the object at a second radiation dosage greater than the first radiation dosage;
generate at least two dark images after scanning the object with the second radiation dosage; and
use the at least two dark images to generate the lag prediction model.

13. A medical imaging system in accordance with claim 11 wherein to periodically update the lag prediction model, said computer further configured to:
acquire at least one dark image; and
update the lag prediction model using the at least one dark image.

14. A medical imaging system in accordance with claim 11 wherein to periodically update the lag prediction model, said computer further configured to:
acquire only one dark image; and
update the lag prediction model using the only one dark image.

15. A medical imaging system in accordance with claim 11 wherein to generate a lag prediction model, said computer further configured to generate a lag prediction model in accordance with:

$$Image_{corr}=Image_{w\_lag}-lag';$$

where:
Image $_{w\_lag}$ is a current fluoro image;

$$lag'=\exp[A+B*\log_e(T)];$$

A is a first model parameter;
B is a second model parameter; and
T is a time beginning from the last high dose exposure that produces lag.

16. A medical imaging system in accordance with claim 12 wherein to generate at least two dark images after scanning the object, said computer further configured to generate a plurality of dark images separated in time by a varying time period.

17. A medical imaging system in accordance with claim 15 wherein said computer is further configured to apply a weighting function to the first model parameter and the second model parameter.

18. A medical imaging system in accordance with claim 15 wherein said computer is further configured to:
determine a first model parameter A in accordance with:

$$A = \log_e(lag_2) - \frac{\log_e(lag_1/lag_2)}{\log_e(T_1/T_2)} * \log_e(T_2);$$

and
determine a second model parameter in accordance with:

$$B = \frac{\log_e(lag_1/lag_2)}{\log_e(T_1/T_2)};$$

where:
$T_1$ is first time at which a dark image including lag is acquired;
$T_2$ is a second time at which a dark image including lag image is acquired.

19. A medical imaging system in accordance with claim 11 wherein said computer is further configured to:
generate a first modified lag image $L'_1$ in accordance with:

$$L'_1 = resampled\left\{L_1 * \frac{G_2}{G_1}\right\};$$

where:
$L_1$=is a first dark image having a lag residue signal;
$G_1$ is a first detector gain; and
$G_2$ is a second detector gain;
generate a second lag image $L_2$; and
use the first lag image and the second lag image to periodically update the lag prediction model.

20. A medical imaging system for processing a fluoroscopic image, said medical system comprising:
a flat panel detector array;
at least one radiation source; and
a computer coupled to said flat panel detector array and said radiation source, said computer configured to:
scan an object at a second radiation dosage with an imaging system including at least one radiation source and at least one detector array;
generate at least two dark images after scanning the object with the second radiation dosage;
use the at least two dark images to generate a lag prediction model;
scan the object at a first radiation dosage;
acquire at least one dark image during the scan at the first radiation dosage; and
periodically update the lag prediction model during the scan using the at least one dark image to generate at least one fluoroscopic image of the object.

21. A computer programmed to:
generate a lag prediction model;
scan an object at a first radiation dosage with an imaging system including at least one radiation source and at least one detector array; and
periodically update the lag prediction model during the scan to generate at least one fluoroscopic image of the object.

22. A computer in accordance with claim 21 wherein to generate a lag prediction model, said computer further programmed to:
scan the object at a second radiation dosage greater than the first radiation dosage;
generate at least two dark images after scanning the object with the second radiation dosage; and
use the at least two dark images to generate the lag prediction model.

23. A computer in accordance with claim 21 wherein to periodically update the lag prediction model, said computer further programmed to:
acquire at least one dark image; and
update the lag prediction model using the at least one dark image.

24. A computer in accordance with claim 21 wherein to periodically update the lag prediction model, said computer further programmed to:
acquire only one dark image; and
update the lag prediction model using the only one dark image.

25. A computer in accordance with claim 21 wherein to generate a lag prediction model, said computer further programmed to generate a lag prediction model in accordance with:

$$Image_{corr}=Image_{w\_lag}-lag';$$

where:
$Image_{w\_lag}$ is a current fluoro image;

$$lag'=\exp[A+B*\log_e(T)];$$

A is a first model parameter;
B is a second model parameter; and
T is a time beginning from the last high dose exposure that produces lag.

26. A method for processing a fluoroscopic image, said method comprising:
receiving a first dosage for a first scan of an object;
scanning the object with the received first dosage;
generating at least one dark image;
generating at least one lag prediction image based on the dark image;
receiving a second dosage for a second scan of the object;
retrieving at least one stored parameter based on the received second dosage; and
incorporating the retrieved parameter into the lag correction model.

27. A method in accordance with claim 26 further comprising scanning the object with the received second dosage.

28. A method in accordance with claim 26 wherein the first dosage is greater than the second dosage.

* * * * *